(12) United States Patent
Pagnacco et al.

(10) Patent No.: US 6,510,749 B1
(45) Date of Patent: Jan. 28, 2003

(54) FORCE MEASURING APPARATUS

(76) Inventors: Guido Pagnacco, 5315 Portland St., Columbus, OH (US) 43235-7661; Elena Oggero, 5315 Portland St., Columbus, OH (US) 43235-7661

( * ) Notice: Subject to any disclaimer, the term of this patent is extended or adjusted under 35 U.S.C. 154(b) by 0 days.

(21) Appl. No.: 09/650,499

(22) Filed: Aug. 29, 2000

(51) Int. Cl.⁷ .................................................. G01D 7/00
(52) U.S. Cl. .................................................. 73/862.041
(58) Field of Search ...................... 73/862.043, 862.041, 73/862.641, 141 A, 862.044; 177/210, 132; 482/52; 182/187; 108/152

(56) References Cited

U.S. PATENT DOCUMENTS

| | | | | |
|---|---|---|---|---|
| 3,741,328 A | * | 6/1973 | Andersson et al. | 177/210 |
| 4,819,750 A | * | 4/1989 | Carnevale | 177/208 |
| 4,984,644 A | * | 1/1991 | Skibinski | 177/132 |
| 5,515,943 A | * | 5/1996 | Antonelli | 182/187 |
| 5,814,740 A | * | 9/1998 | Cook et al. | 73/862.641 |
| 6,222,137 B1 | * | 4/2001 | Handford | 177/126 |
| 6,337,446 B1 | * | 1/2002 | Hulburt et al. | 177/126 |

* cited by examiner

*Primary Examiner*—Max Noori
(74) *Attorney, Agent, or Firm*—Parsons & Goltry; Michael W. Goltry; Robert A. Parsons

(57) ABSTRACT

Force measuring apparatus that includes a platform and a base for supporting the platform above a supporting surface at only three spaced-apart points. The platform consists of first and second working portions. The first working portion has a first area and the second working portion has a second area. The first area is larger than the second area. The first area is limited to accommodate only an on-line stance. The first and second areas together are limited to accommodate only an in-line stance. The force measuring apparatus incorporates sensor apparatus for sensing loads exerted against the first and second areas.

16 Claims, 3 Drawing Sheets

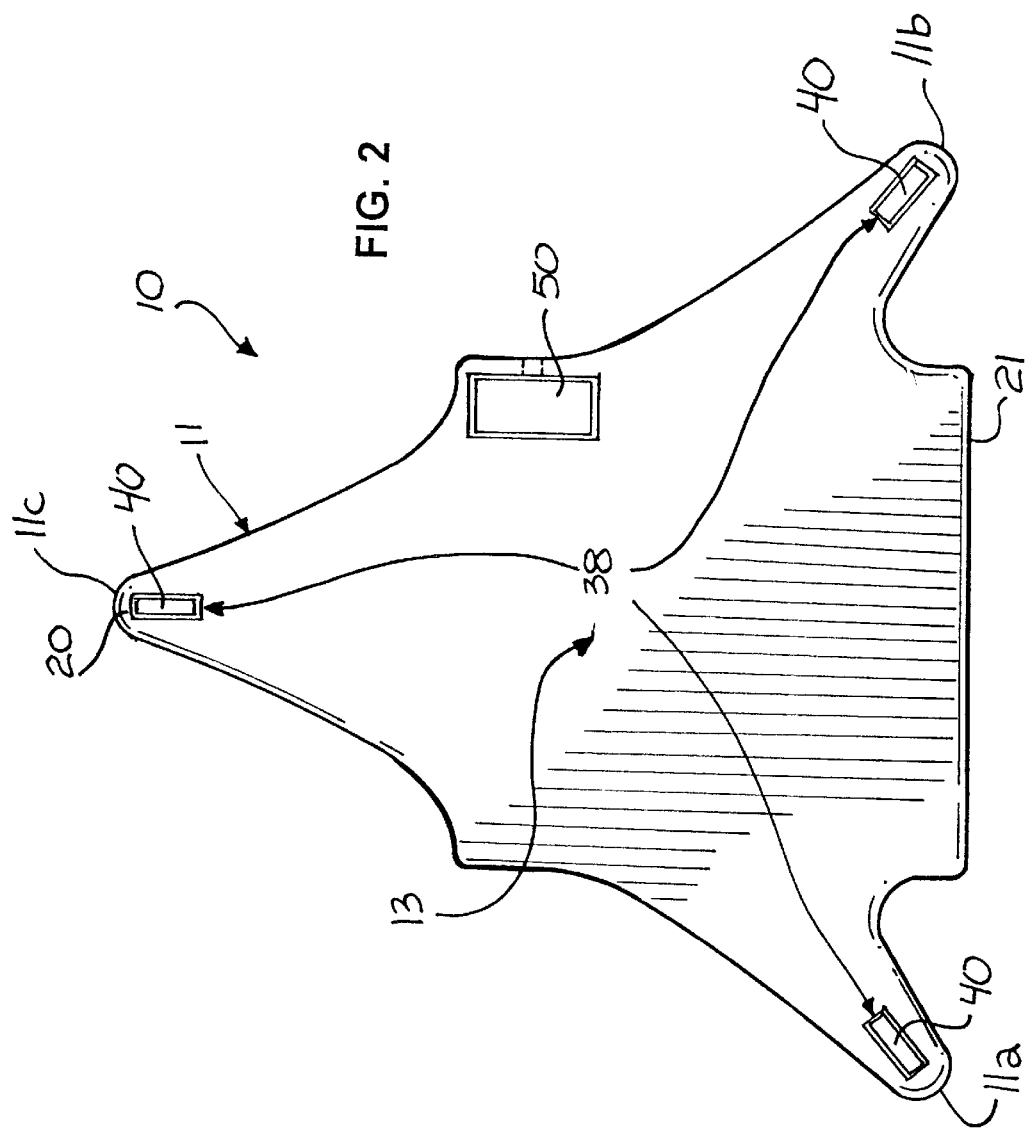

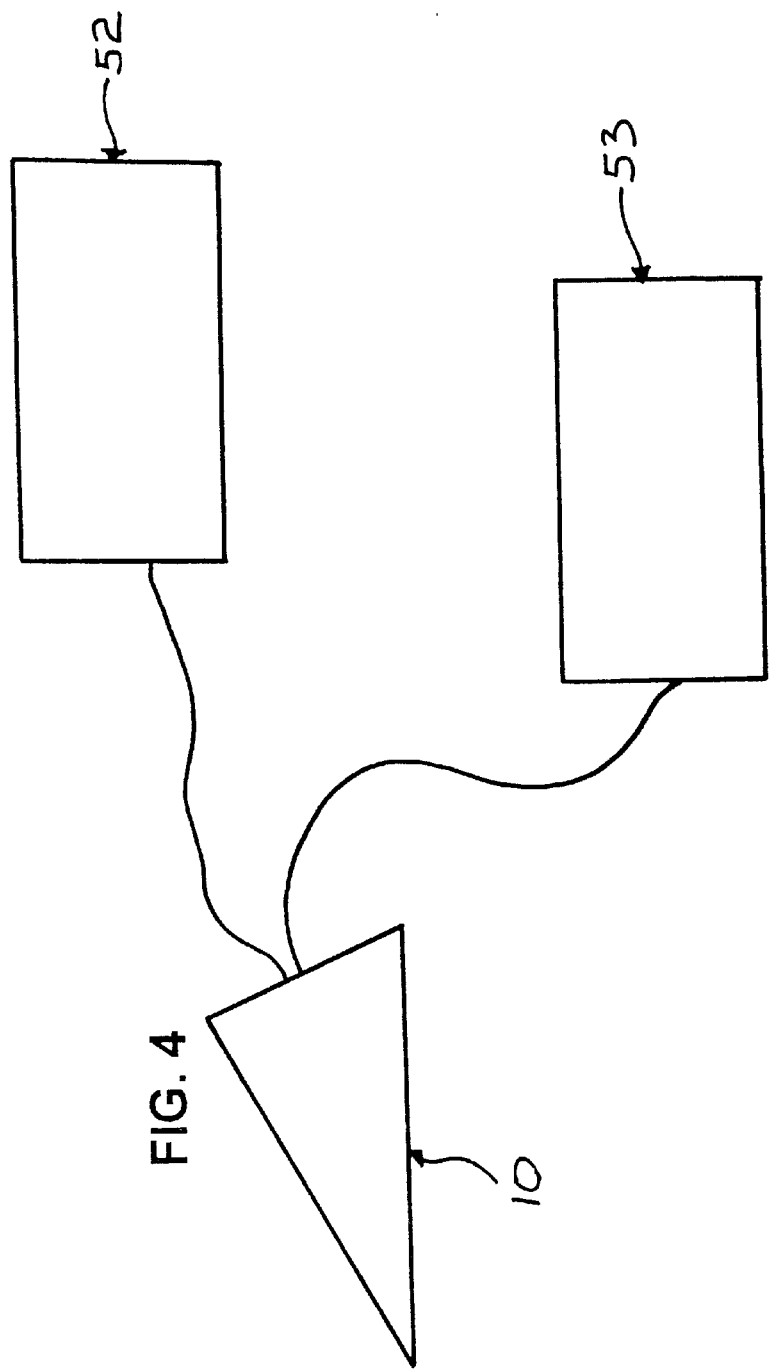

FORCE MEASURING APPARATUS

FIELD OF THE INVENTION

This invention relates to apparatus and methods for measuring forces.

BACKGROUND OF THE INVENTION

Force platforms are devices that employ a support surface and an arrangement of sensors, which are configured to measure force components and moments along one or more axes and along one or more associated orthogonal axes. As a matter of usefulness, force platforms are commonly used in biomechanics, medical research, orthopedics, rehabilitation evaluation, prosthetics, engineering and other clinical or research fields for measuring the forces exerted by individual in varying forms of stance. Having the ability to measure and understand the forces of an individual in varying forms of stance is very useful, as it allows medical and clinical specialists to quantify physical disabilities and abilities, especially with the elderly and patients who suffer from limited or impaired going-on-foot movement.

In an effort to improve the state of the art, skilled artisans devote considerable time and resources toward enhancing the sensing architecture of force platforms. However, existing force platforms are still heavy and large and difficult to move, must be installed at a fixed or permanent location and consume a large amount of electrical power. Thus, there is a need for an improved force platform that is light and portable, easily installed at different locations, energy efficient and that is minimally sized yet configured to accommodate different forms of stance.

SUMMARY OF THE INVENTION

The above problems and others are at least partially solved and the above purposes and others realized in new and improved force measuring apparatus. The force measuring apparatus is preferably comprised of a substantially triangular support structure having working portions for accommodating on-line and in-line stances, sensor apparatus for measuring loads exerted against the working portions and a base for supporting the support structure above a supporting surface at only three spaced-apart points. The sensor apparatus is preferably associated with the base, the base preferably includes three spaced-apart feet, and the sensor apparatus is adapted and arranged for sensing loads along one or more axes.

BRIEF DESCRIPTION OF THE DRAWINGS

Referring to the drawings:

FIG. 2 is a bottom plan view of the apparatus of FIG. 1;

FIG. 3 is an end view of the apparatus of FIG. 1; and

FIG. 4 is a schematic representation of a system including the apparatus of FIG. 1 and associated external devices for supplying power to, communicating with and receiving and processing data from the apparatus.

DETAILED DESCRIPTION OF A PREFERRED EMBODIMENT

Figure 1:
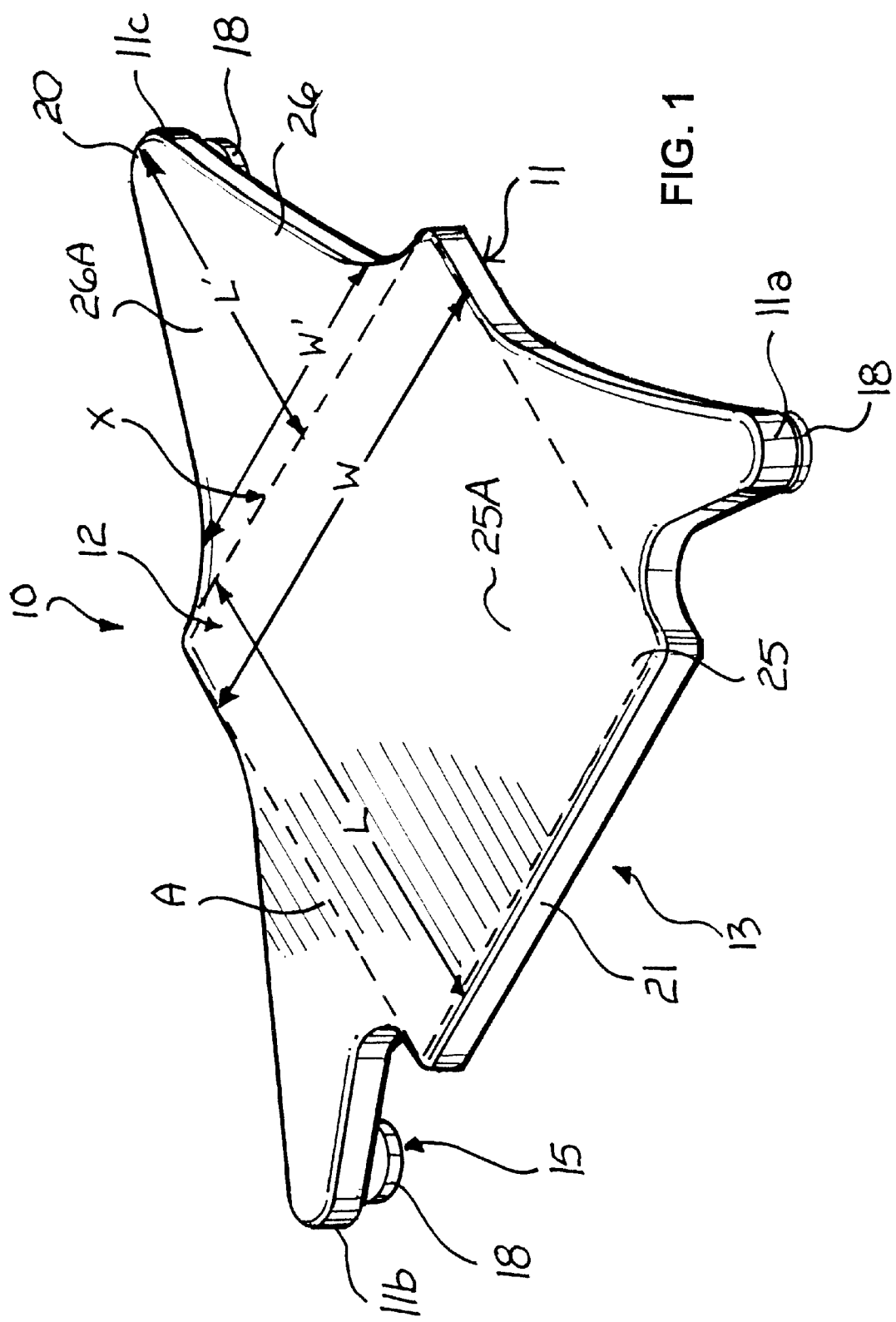
FIG. 1 is a perspective view and partial schematic layout of apparatus for sensing and measuring loads in accordance with the present invention.

Turning to the drawings, FIG. 1 illustrates a perspective view of apparatus 10 for accommodating individuals in varying forms of stance, such as on-line and in-line stances, and for sensing and measuring associated loads or forces. Apparatus 10 is comprised of a platform on support structure 11 that has or is otherwise equipped with or associated with a base 15 for supporting support structure 11 above a supporting surface at only three points. Support structure 11 has a substantially flat form, defines opposing major faces 12 and 13 and is substantially or generally triangular in shape. In this regard, support structure 11 defines triangulated extremities 11a,11b,11c. Base 15 is generally defined by or otherwise located at extremities 11a,11b,11c and, in this embodiment, includes a triangular arrangement of spaced-apart feet 18 (see also FIG. 3). Each one of feet 18 is fixed or otherwise coupled to support structure 11 and extends away from major face 13 at one of extremities 11a,11b,11c. As a matter of definition, feet 18 may each be considered one of a)part of and b)an extension of a respective one of extremities 11a,11b,11c, and extremities 11a,11b,11c, may each be considered a feature of base 15. In this spirit, feet 18 can be formed with or otherwise defined by support structure 11 proximate extremities 11a,11b,11c, embedded into support structure 11 proximate extremities 11a,11b,11c, screwed or otherwise fitted into support structure 11 proximate extremities 11a,11b,11c, with a suitable male/female engagement mechanism or otherwise fixed in place to support structure 11 proximate extremities 11a,11b,11c, with one or more of screws, rivets, nails, adhesive, etc. Support structure 11 is preferably constructed of one or more non-conductive and relatively light natural and/or synthetic materials such as plywood, laminated or united superimposed layers of cellulose and/or fiber reinforced materials such as plastic or non-conductive metal composites, etc. Furthermore, support structure 11 may be constructed as a single or substantially unitary element, or constructed from an assembly of various parts.

With continuing reference to FIG. 1, support structure 11 includes opposing ends 20 and 21 and defines an overall length generally from end 20 to end 21. For ease of discussion, end 20 is considered a leading end and end 21 is considered a trailing end. The substantially triangular shape of support structure 11 defines substantially only two working portions 25 and 26 between leading and trailing ends 20 and 21, which is important as this minimizes the overall size and weight of apparatus 10 as will be more fully explained later in this specification. Working portions 25 and 26 define working surfaces 25A and 26A of major face 12, which are for accommodating individuals in varying forms of stance. Outside of working portions 25 and 26, the remaining features of support structure 11 leading to and defining extremities 11a,11b are too small and/or not configured to be or capable of being stood upon in any form of stance. Working portion 25 is substantially square as generally denoted in FIG. 1 by a dotted outline A. Working surface 25A is, accordingly, substantially square and is of a size that is sufficient to accommodate only an on-line stance. Working portion 26 extends away from working portion 25 and extremities 11a and 11b and toward extremity 11c and is a substantial triangle as shown. Working surface 26A is, accordingly, substantially triangular and is of a size that is sufficient to accommodate an in-line stance in cooperation with at least part of working surface 25A. In accordance with this specification, an on-line stance is defined herein as a side-by-side and substantially side-by-side positioning of the two feet of a human subject with the feet together, shoulder-width apart, somewhat angled relative to one another and even partially offset, and an in-line stance is a tandem or heel-to-toe stance of the two feet of a human subject.

Working portion 25 defines a maximum width W and a maximum length L that cooperate and define the area of working surface 25A. Length L extends from trailing end 21 to a location X intermediate leading and trailing ends 20 and 21. Location X is a point substantially where working portions 25 and 26 meet. Working portion 26 defines a maximum width W' and a maximum length L' that cooperate and define the area of working surface 26A. Length L' extends from leading end 20 to location X.

As previously mentioned, working portion 25 is sufficiently sized for accommodating only an on-line stance, and working portion 26 is sufficiently sized to accommodate an in-line stance in cooperation with at least part of working surface 25A. In terms of an in-line stance, it will be understood that a foot is placed upon working surface 26A and another foot is placed upon working surface 25A so as to be heel-to-toe. An aspect ratio defined by a ratio of length L of working portion 25 to length L' of working portion 26. This aspect ratio is preferably between 1:1 and 3:1 and preferably 2:1. This aspect ratio range ensures that working surface 26A can accommodate an in-line stance in cooperation with at least part of working surface 25A while minimizing the overall length of support structure 11 from leading end 20 to trailing end 21, minimizing the overall width of support structure 11 that its substantially triangular shape provides and, accordingly, minimizing the overall weight and size of support structure 11. In view of this, apparatus 10 is very portable and otherwise easily stored and carried or transported from place to place. Furthermore, because base 15 engages a supporting surface at only three points, support structure 11 will always be stable against a supporting surface, regardless of whether the supporting surface is irregular or angled, etc.

Looking to FIG. 2, apparatus 10 is equipped with sensor apparatus 38 for sensing loads exerted against working surfaces 25A and 26A. Sensor apparatus 38 comprises a plurality of sensors or load cells 40 and preferably three, and less or more may be employed. Load cells 40 each comprise a strain gauge, a piezoelectric cell, a transducer or any suitable device or apparatus capable of measuring loads along one or more axes, such as one or more of the x, y and z axes and/or one or more associated moments and/or orthogonal axes. Sensors 40 can be embedded into or otherwise associated with or mounted to support structure 11 in a potentially vast number of ways for allowing them to detect and measure loads applied to working surfaces 25A and 26A. In accordance with a preferred embodiment, sensors 40 are each mounted or otherwise fixed to support structure 11 at one of extremities 11a,11b,11c. Each one of sensors 40 is more particularly and preferably adapted and arranged or associated with or as part of base 15 in such a way so that the loads born by base 15 and more particularly feet 18 against a supporting surface are felt at sensors 40. In a specific embodiment, sensors 40 may each be fastened or fixed to or incorporated as part of support structure 11 and each one of feet 18 engaged, fixed or otherwise coupled directly to one of sensors 40. In this manner, sensors 40 are considered part of or otherwise associated with base 15.

Regarding FIG. 2, support structure is provided with a processor 50. Processor 50 is preferably carried by support structure 11 and it may be located elsewhere, is programmable with a dedicated or remote input device, and is configured to communicate with and receive data from sensor apparatus 38 over a wired and/or wireless data transfer and communication architecture. In response to sensing loads, sensor apparatus 38 generates load data and sends the load data to processor 50. The load data taken by sensor apparatus 38 is normally analog and, thus, sent to processor in the form of analog signals. Processor 50 is preferably equipped with analog-to-digital (A/D) conversion capability, which converts the analog signals into digital data or signals, which are sent to another device or computer or otherwise capable of being accessed by another device or computer. Processor 50 may be equipped or otherwise associated with storage if desired. The A/D conversion capability of circuitry 50 is important because it reduces overall energy consumption, reduces or otherwise eliminates the noise normally associated with analog signals, allows for the use of a more compact or small associated electrical infrastructure as compared to analog infrastructures, and eliminates the need for a dedicated or external A/D conversion device.

To provide an operator with sensible data that reflects the load data taken by sensor apparatus 38, processor 50 may be associated with a conventional output device such as a conventional illuminated display or screen such as a flat panel display or the like. The display can be carried by support structure 11 or located elsewhere. To allow the load data taken by sensor apparatus 38 to be displayed and manipulated, apparatus 10 may also or alternatively be employed with computer or computerized device having display and input and output capabilities. This computer may be formed or otherwise incorporated with support structure 11 or, as shown in FIG. 4, provided as an external device denoted generally by the reference character 52. Device 52 may comprise a desk-top computer, a laptop computer or other form of portable computer and is preferably digital for providing exemplary signal and data processing and storage capabilities. The data communication or coupling between device 52 and processor 50 can be wired and/or wireless. In this example, apparatus 10 and device 52 may comprise discrete elements and configured to communicate with one another over wired and/or wireless communication pathways such as a local or central computerized network or telephony architecture, and may otherwise be configured to plug into one another with one or more physical plug couplings or the like. As a matter of example, apparatus 10 may be provided with electrical power by way of device 52, by virtue of a self-contained power source such as a nickel-cadmium battery or other form or battery whether rechargeable, or perhaps coupled to an external power source 53 as shown generally in FIG. 4, which may comprise a dedicated power source or a self-contained power source.

Thus, a new and improved apparatus 10 for measuring forces is disclosed, which incorporates a physical geometry that is minimally-sized yet capable of accommodating the primary stances used to evaluate standing sway, namely, on-line and in-line stances. By measuring the forces exerted by an individual standing upon one or more of working surfaces 25A and 26A of apparatus 10, the sway of the individual can be understood, which allows clinical personnel to define the appropriate care the individual may need, to identify appropriate prosthetic devices for correcting stance abnormalities or to simply identify individuals that are at risk of falling when walking or when otherwise engaging in normal going-on-foot activities. Apparatus 10 is configured to be supported above a supporting surface at only three points so that it is always stable and resistant to tipping and rocking, and incorporates analog-to-digital circuitry for conserving electrical power. Due to the geometry of apparatus 10 as disclosed in this specification, apparatus 10 is light, portable and easy to carry, and need not be fixed to a permanent supporting structure as in the prior art.

Because apparatus 10 is portable, it is preferably constructed and arranged to be resistant to water and other environmental elements.

The invention has been described above with reference to one or more preferred embodiments. However, those skilled in the art will recognize that changes and modifications may be made in the described embodiments without departing from the nature and scope of the invention. Various changes and modifications to one or more of the embodiments herein chosen for purposes of illustration will readily occur to those skilled in the art. To the extent that such modifications and variations do not depart from the spirit of the invention, they are intended to be included within the scope thereof, which is assessed only by a fair interpretation of the following claims.

Having fully described the invention in such clear and concise terms as to enable those skilled in the art to understand and practice the same, the invention claimed is:

What is claimed is:

1. Force measuring apparatus comprising:
    a platform having leading and trailing ends and a base for supporting the platform above a supporting surface, the platform consisting of a first working portion disposed toward the trailing end of the platform and a second working portion disposed toward the leading end of the platform, the first working portion having a length and a first area and the second working portion having a length and a second area, the first area being larger than the second area;
    an overall length of the platform from the leading end thereof to the trailing end thereof;
    an aspect ratio defined by a ratio of the length of the first working portion relative to the length of the second working portion, the aspect ratio being at least 1:1;
    the first area limited to accommodate only an on-line stance;
    the first and second areas together limited to accommodate only an in-line stance; and
    sensor apparatus for sensing loads exerted against the first and second areas:
    the aspect ratio ensuring that the second area can accommodate an in-line stance in cooperation with at least part of the first area while minimizing the overall length of the platform from the leading end thereof to the trailing end thereof.

2. Force measuring apparatus of claim 1, wherein the sensor apparatus is associated with the base.

3. Force measuring apparatus of claim 1, wherein the base includes three spaced-apart feet.

4. Force measuring apparatus of claim 1, wherein the sensor apparatus is capable of sensing loads along at least one of a single axis and multiple axes.

5. Force measuring apparatus of claim 1, wherein the sensor apparatus comprises a plurality of sensors each for sensing loads along at least one of a single axis and multiple axes.

6. Force measuring apparatus of claim 1, wherein the first area is substantially square.

7. Force measuring apparatus of claim 1, wherein the second area is substantially triangular.

8. Force measuring apparatus comprising:
    a platform having leading and trailing ends and further consisting of
        a substantially square first working portion having a length and a substantially square first area, the first working portion disposed toward the trailing end of the platform, and
        a substantially triangular second working portion extending away from the first working portion and having a length and a substantially triangular second area, the second working portion disposed toward the leading end of the platform,
        wherein the first area is larger than the second area and the platform is capable of measuring forces applied against the first and second areas;
    an overall length of the platform from the leading end thereof to the trailing end thereof;
    an aspect ratio defined by a ratio of the length of the first working portion relative to the length of the second working portion, the aspect ratio being at least 1:1;
    a base for supporting the platform above a supporting surface;
    the first area limited to accommodate only an on-line stance; and
    the first and second areas together limited to accommodate only an in-line stance;
    the aspect ratio ensuring that the second area can accommodate an in-line stance in cooperation with at least part of the first area while minimizing the overall length of the platform from the leading end thereof to the trailing end thereof.

9. Force measuring apparatus of claim 8, wherein the base comprises three spaced-apart feet.

10. Force measuring apparatus of claim 8, wherein the force platform is further capable of sensing loads applied to the first and second areas along single and multiple axes.

11. Force measuring apparatus comprising:
    a platform having leading and trailing ends and further consisting of
        a substantially square first working portion having a length and a first area, the first working portion disposed toward the trailing end of the platform, and
        a substantially triangular second working portion extending away from the first working portion and having a length and a second area, the second working portion disposed toward the leading end of the platform,
        wherein the first area is larger than the second area and the platform is capable of measuring forces applied against the first and second areas;
    an overall length of the platform from the leading end thereof to the trailing end thereof;
    an aspect ratio defined by a ratio of the length of the first working portion relative to the length of the second working portion, the aspect ratio being at least 1:1;
    a base for supporting the platform above a supporting surface at only three spaced apart points;
    the first area limited to accommodate only an on-line stance;
    the first and second areas together limited to accommodate only an in-line stance; and
    sensor apparatus for measuring loads exerted against the first and second areas;
    the aspect ratio ensuring that the second area can accommodate an in-line stance in cooperation with at least part of the first area while minimizing the overall length of the platform from the leading end thereof to the trailing end thereof.

12. Force measuring apparatus of claim 11, wherein the sensor apparatus is associated with the base.

13. Force measuring apparatus of claim 11, wherein the base comprises three spaced-apart feet.

14. Force measuring apparatus of claim 11, wherein the sensor apparatus is capable of sensing loads along at least one of a single axis and multiple axes.

15. Force measuring apparatus of claim 11, wherein the sensor apparatus comprises a plurality of sensors each for sensing loads along at least one of a single axis and multiple axes.

16. Force measuring apparatus of claim 11, the sensor apparatus for providing load data of the measured loads in the form of analog signals, further including a processor for receiving the analog signals and converting the analog signals to digital signals.

* * * * *